United States Patent
Stauber (10) Patent No.: US 8,142,416 B2
(45) Date of Patent: Mar. 27, 2012

(54) STEERABLE SURGICAL GUIDE WIRE INTRODUCER

(76) Inventor: Marshall Ephraim Stauber, Hollywood, FL (US)

( * ) Notice: Subject to any disclaimer, the term of this patent is extended or adjusted under 35 U.S.C. 154(b) by 0 days.

(21) Appl. No.: 12/752,552

(22) Filed: Apr. 1, 2010

(65) Prior Publication Data

US 2010/0298814 A1    Nov. 25, 2010

Related U.S. Application Data

(63) Continuation-in-part of application No. 11/309,701, filed on Sep. 15, 2006, now abandoned.

(51) Int. Cl.
*A61M 25/09* (2006.01)
(52) U.S. Cl. .................... 604/528; 604/164.01
(58) Field of Classification Search .......... 604/528, 604/164.01, 164.13, 164.02, 164.04, 264, 604/96.01, 529, 165.01, 165.02, 165.04; 600/585

See application file for complete search history.

(56) References Cited

U.S. PATENT DOCUMENTS

| | | | |
|---|---|---|---|
| 5,066,285 A | 11/1991 | Hillstead | |
| 5,267,756 A | 12/1993 | Molee | |
| 5,380,290 A | 1/1995 | Makower et al. | |
| 5,432,329 A | 7/1995 | Colgate, Jr. et al. | |
| 5,673,338 A | 9/1997 | Densberger | |
| 5,971,432 A | 10/1999 | Gagnon et al. | |
| 6,053,904 A | 4/2000 | Scribner | |
| 6,134,467 A | 10/2000 | Ouchi | |
| 6,250,549 B1 | 6/2001 | DeFabio, Jr. | |
| 6,309,690 B1 | 10/2001 | Brogger | |
| 6,311,042 B1 | 10/2001 | DeSchrijver | |
| 6,424,728 B1 | 7/2002 | Ammar | |
| 6,475,634 B1 | 11/2002 | Lam | |
| 6,591,252 B1 | 7/2003 | Young | |
| 6,626,869 B1 | 9/2003 | Bint | |
| 6,679,873 B2 * | 1/2004 | Rabiner et al. | 604/528 |
| 6,706,017 B1 | 3/2004 | Dulguerov | |
| 2001/0033676 A1 | 10/2001 | Noyes | |
| 2001/0049606 A1 | 12/2001 | Lucarelli | |
| 2003/0088153 A1 | 5/2003 | Carrillo, Jr. et al. | |
| 2003/0220885 A1 | 11/2003 | Lucarelli | |
| 2004/0236214 A1 | 11/2004 | Opie et al. | |
| 2005/0131341 A1 * | 6/2005 | McGuckin et al. | 604/43 |
| 2008/0071223 A1 | 3/2008 | Stauber | |

FOREIGN PATENT DOCUMENTS

EP    0643364    3/1995

* cited by examiner

*Primary Examiner* — Jackie Ho
*Assistant Examiner* — Michael J Anderson
(74) *Attorney, Agent, or Firm* — McHale & Slavin, P.A.

(57) ABSTRACT

A guide wire introducer with integrated wire steering function for treating bone. The guide wire employed with the introducer includes a bore material that is a psuedoelastic metal alloy, such as Nitinol. This introducer has a chamfered tip with the complement of the outer construction including a uniform narrow outer diameter enabling insertion into soft tissue and bone with a guide wire therein. The chamfered tip of the introducer incorporates as integrated slit that enables the steering function of the introducer. Additionally, the outer surface of the introducer incorporates a radiolucent notch for radial position reference.

4 Claims, 8 Drawing Sheets

STEERABLE SURGICAL GUIDE WIRE INTRODUCER

RELATED APPLICATIONS

This application is a continuation-in-part of U.S. patent application Ser. No. 11/309,701, filed Sep. 15, 2006 now abandoned, entitled "STEERABLE SURGICAL GUIDE WIRE INTRODUCER", the entirety of which is incorporated herein by reference.

FIELD OF INVENTION

This invention relates to the field of medical devices that are used for enabling percutaneous minimally invasive access for the treatment of cancellous bone using guide wire directed devices.

BACKGROUND OF THE INVENTION

Guide wires can be used in a range of surgical procedures to reduce the invasiveness of the respective procedure. For example, there are surgical procedures to correct injuries and maladies of the bone through the introduction of a flexible to semi-rigid/rigid catheter or tube that can be guided by a surgical guide wire. In a specific example, this invention can be employed in the surgical correction of a vertebral compression fracture injury that can be treated with bone cement. In this specific example, a semi-rigid tube or catheter is introduced into the volume of the compression fracture of the vertebral body and a balloon or bladder is introduced through a catheter or tube into the cancellous bone and inflated to correct the kyphosis induced by the compression fracture of a vertebral body. Afterwards the bladder or balloon is removed, and then bone cement is introduced using a catheter or tube. The guidance of catheter(s) or tube(s) in the example above is critical, and can be obtained by employing the use of a guide wire that has been introduced and steered to the optimal location by the provided invention.

SUMMARY OF THE INVENTION

The provided invention consists of a Guide Wire Introducer with integrated wire steering function for treating bone. The introducer is designed to employ a guide wire with a core material that behaves like a psuedoelastic metal alloy, such as Nitinol. This introducer is tubular and rigid with a chamfered tip at its distal end that enables introduction into soft tissue, and limited introduction into bone. The majority of the tubular introducer has a maximum outer diameter that is approximately three millimeters in diameter, for the typical vertebral body application. The exact maximum outer diameter for the introducer varies minutely according to specific application. Most of the outer surfaces are the complement of the outer construction other than the chamfered tip at the distal end, and consist of the uniform narrow outer diameter indicated above, a characteristic that enables insertion into soft tissue and bone with a guide wire within the introducers' inner tubular portion. Within the chamfered tip of the introducer and incorporated into the body of the introducer is an integrated slit that enables the steering function of the introducer by entrapping the guide wire. Within four to eight millimeters of the slit is a radiolucent notch incorporated within the outer surface, for radial position referencing that assists the surgeon in determining the radial position of the slit.

Accordingly it is an objective of the instant invention to enable or enhance procedures that would benefit from the use of a steerable guide wire with emphasis on procedures involving the guidance of a catheter or tube into cancellous bone.

It is a further objective of the instant invention to provide a device which enables a surgical guide wire to be steered or moved in different directions as it is introduced into cancellous bone.

It is still yet another objective of the invention to provide a device which utilizes pre-bent surgical guide wires to enable the guide wires to be steered or moved in different directions at it is introduced into cancellous bone.

Other objectives and advantages if this invention will become apparent from the following description taken in conjunction with any drawings wherein are set forth, by way of example, certain embodiments of this invention. Any drawings contained herein constitute a part of this specification and include exemplary embodiments of the present invention and illustrate various objects and features thereof.

DRAWINGS—REFERENCE NUMERALS

1 Steerable Surgical Guide Wire Introducer.
2 Chamfered tip.
7 Integrated slit.
8 Radial referencing notch.
9 Guide Wire inserted into introducer.
10 Guide Wire bend entrapment within slit.
11 Simplified representation of a vertebra with Steerable Surgical Guide Wire Introducer.
12 and 14 Walls of the introducer.
16 Cavity in the introducer.
18 and 20 Surfaces of wall 12.
22 and 24 Surfaces of wall 14.
26 and 28 End portions of walls 12 and 14.

DETAILED DESCRIPTION

The embodiments of the provided invention are employable in the applications as indicated above in addition to all those that can be commonly inferred from those indicated above. This invention enables or enhances procedures that would benefit from the use of a steerable guide wire 9 with emphasis on procedures involving the guidance of a surgical guide wire that has been introduced and advanced into cancellous bone.

In the instant invention, the chamfered tip of the introducer 1 incorporates an integrated slit 7, at one end, that enables the steering function of the introducer. This introducer 1 has a chamfered tip 2 with the complement of the outer construction having a uniform narrow outer diameter preferably of approximately 3 mm for the typical application, enabling insertion into soft tissue and to a limited extent in bone, with a guide wire within its inner cavity. Additionally, the outer surface incorporates a radiolucent notch 8 for radial position reference. While the guide wire introducer is preferably tubular, other shapes are also possible.

Suitable material such as surgical stainless steel or similar material is desired in the production of the preferred embodiment of the introducer to provide for the desired strength, flexibility, and fatigue life.

Figure 1:
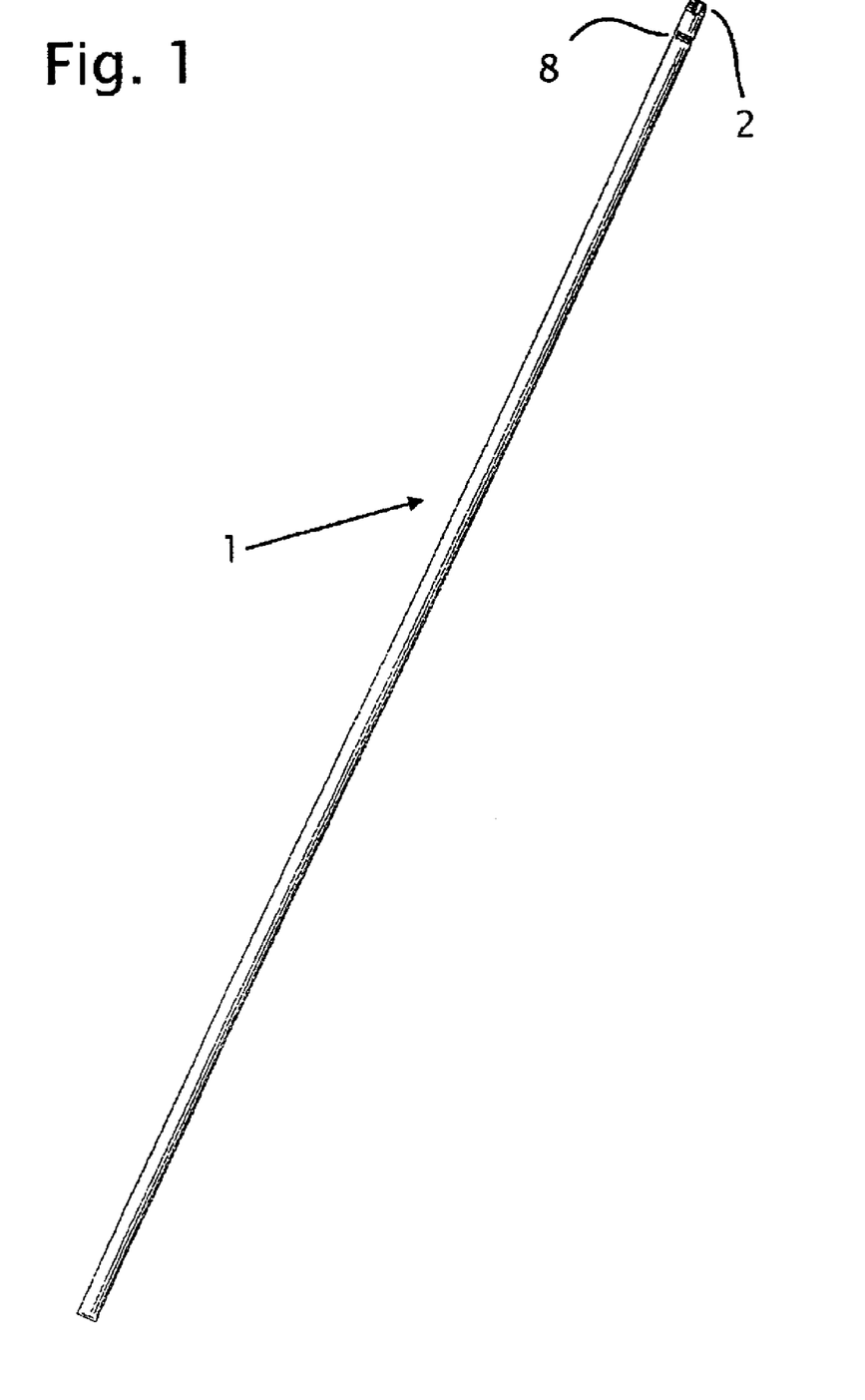
FIG. 1 shows the entire surgical guide wire introducer with the integrated slit and radiolucent notch exposed.
Figure 2:
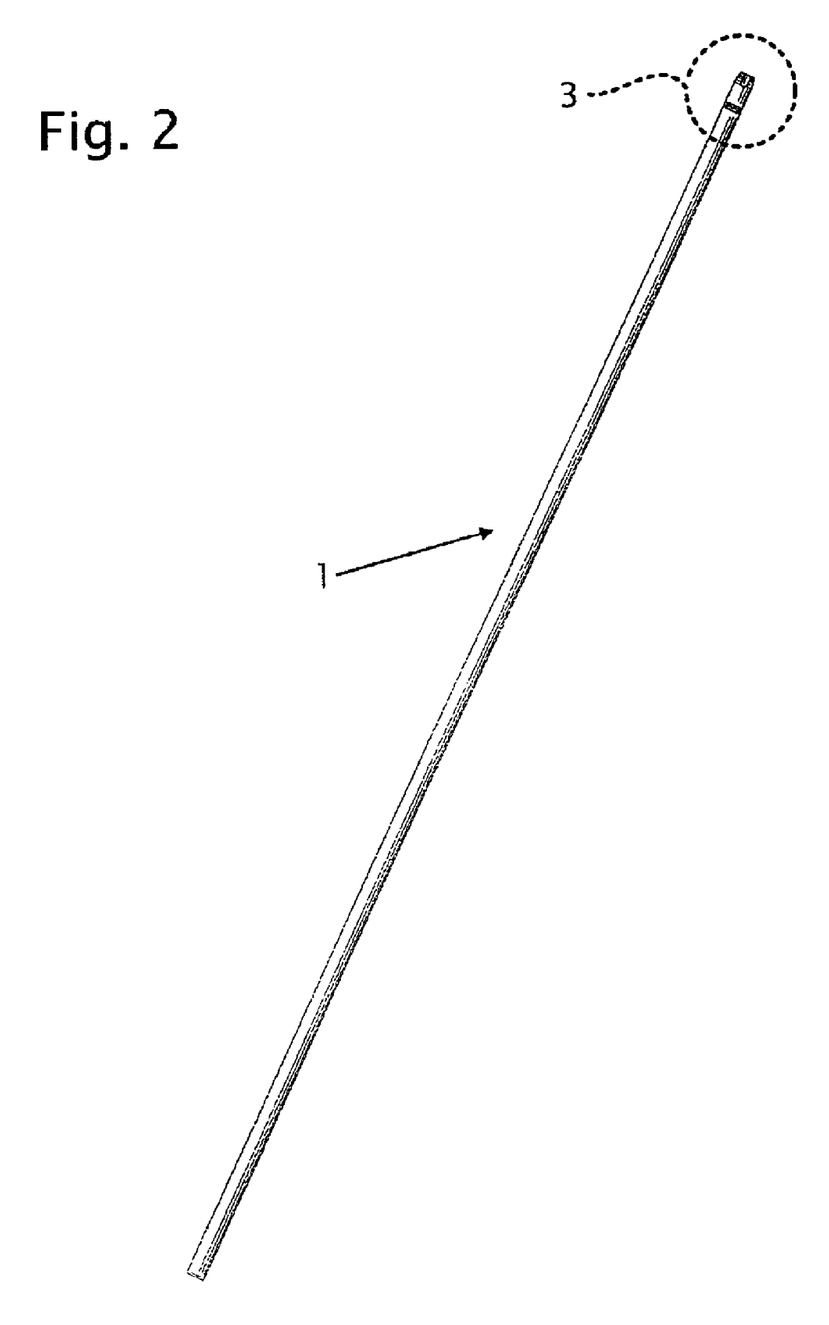
FIG. 2 shows the extent of the enlarged partial view seen in FIG. 3.
Figure 3:
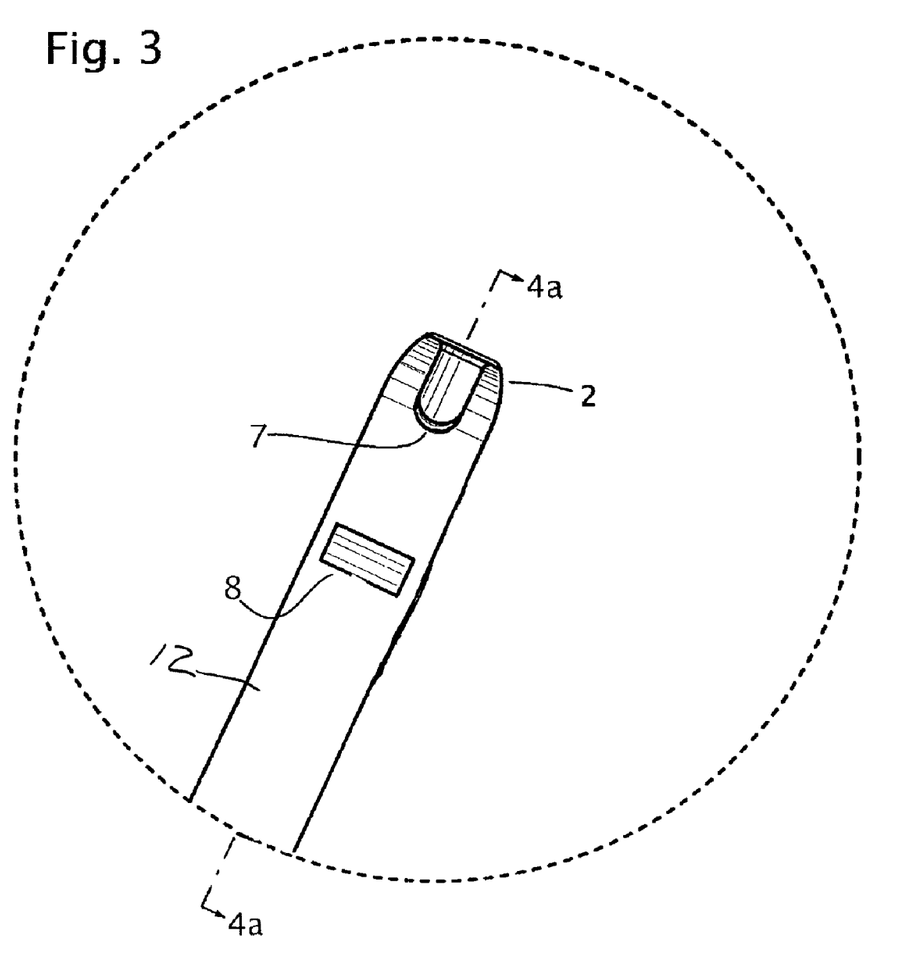
FIG. 3 is an enlarged view of the radiolucent referencing notch and the introducer integrated slit.

The guide wire introducer with integrated wire steering function for treating bone, is shaped as a long thin tubular structure 1 with a psuedoelastic surgical guidewire 9 carried within. The guide wire introducer 1 is an elongate member having two substantially flat longitudinally extending walls 12 and 14, FIGS. 3-4C. Walls 12 and 14 are substantially flat along their longitudinal dimension. Walls 12 and 14 have a longitudinal dimension which extends along the length of the guide wire introducer and a lateral dimension which is substantially perpendicular to the longitudinal dimension. Walls 12 and 14 are substantially parallel to each other and are spaced from each other. Internal cavity 16 is formed by the spaced apart walls 12 and 14. Wall 12 includes an inner surface 18 and an outer surface 20. Wall 14 includes an inner surface 22 and an outer surface 24. Each of surfaces 18, 20, 22 and 24 has longitudinal and lateral dimension which correspond to the longitudinal and lateral dimensions of walls 12 and 14. Cavity 16 houses the guide wire 9 which is employed with the introducer and includes a core material that is a psuedoelastic metal alloy, such as Nitinol or similar material. When employed in the treatment of the vertebral body for example, a pilot hole may or may not be drilled depending on the approach to the vertebral body and condition of the vertebral body during the procedure when the provided invention is employed.

Figure 4A:
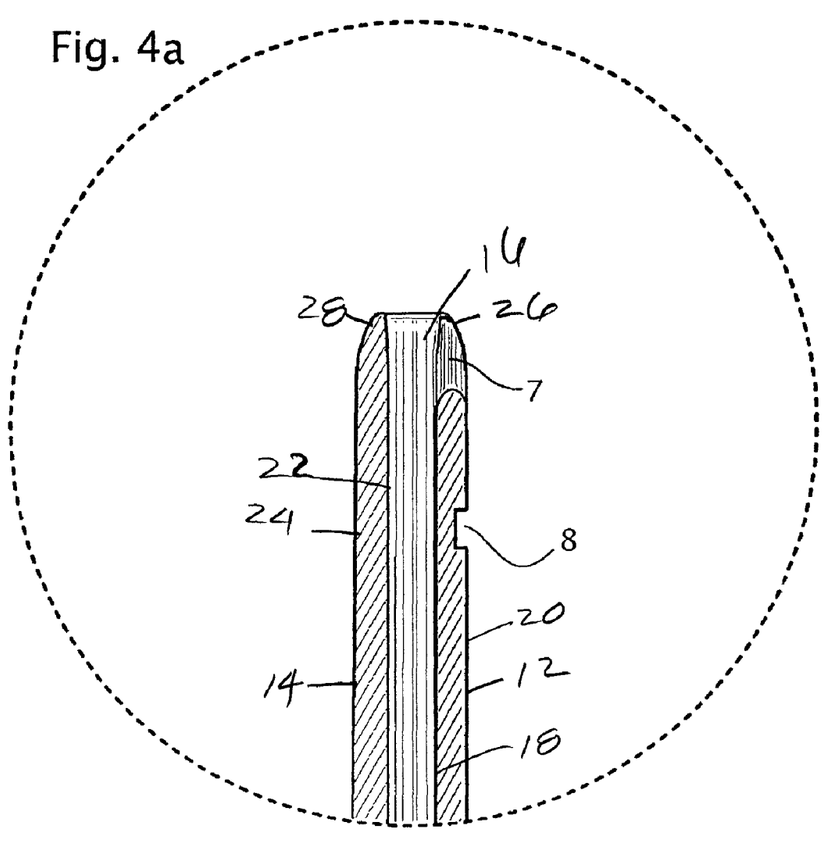
FIG. 4a is a sectional view of FIG. 3, along line 4a-4a, showing a profile view of the radiolucent notch. In addition, the bore of the instrument and the integrated slit are also shown.
Figure 4B:
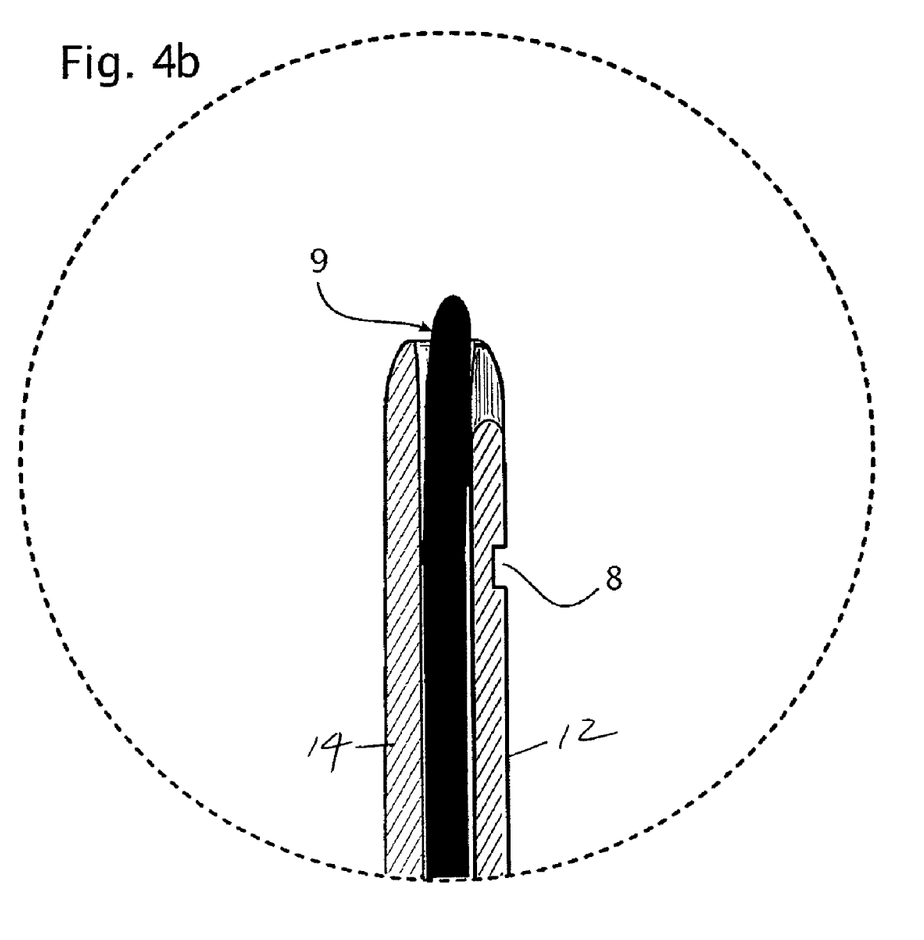
FIG. 4b is a sectional view of FIG. 3 showing a profile view of the radiolucent notch with a surgical guide wire shown in the bore of the instrument. This illustration shows a view of a surgical guide wire before it is advanced to the extent were its strategic bend is within range of the integrated slit.
Figure 4C:
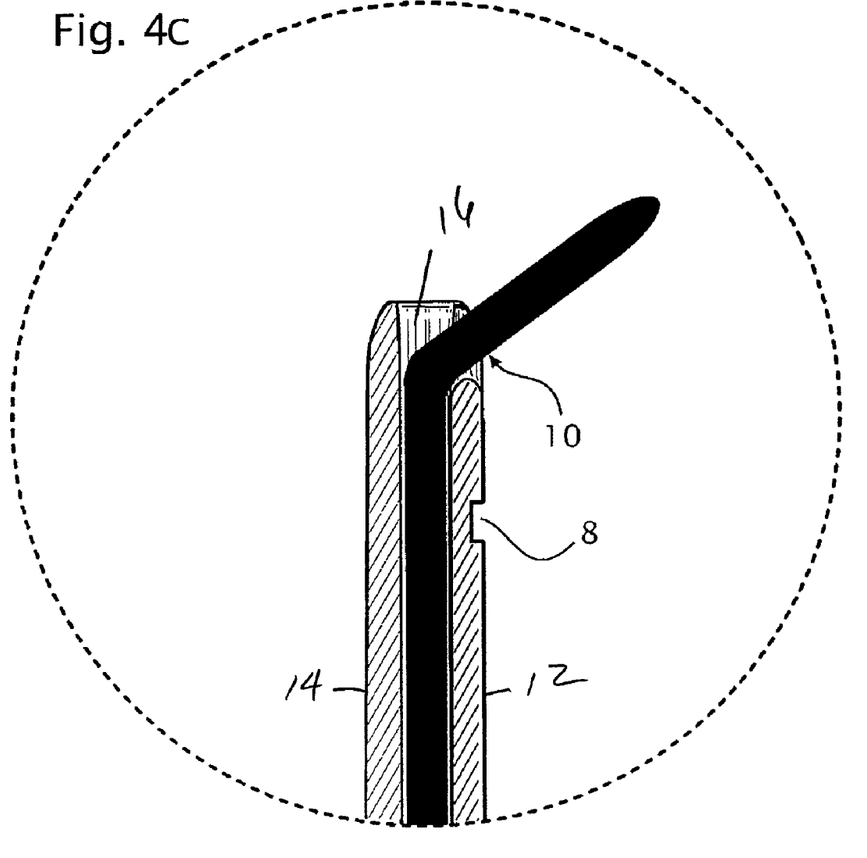
FIG. 4c is a sectional view of FIG. 3 showing a profile view of the radiolucent notch with a surgical guide wire shown in the bore of the instrument. This illustration shows a view of a surgical guide wire as it is advanced to the extent were its strategic bend slides into the integrated slit.
Figure 5:
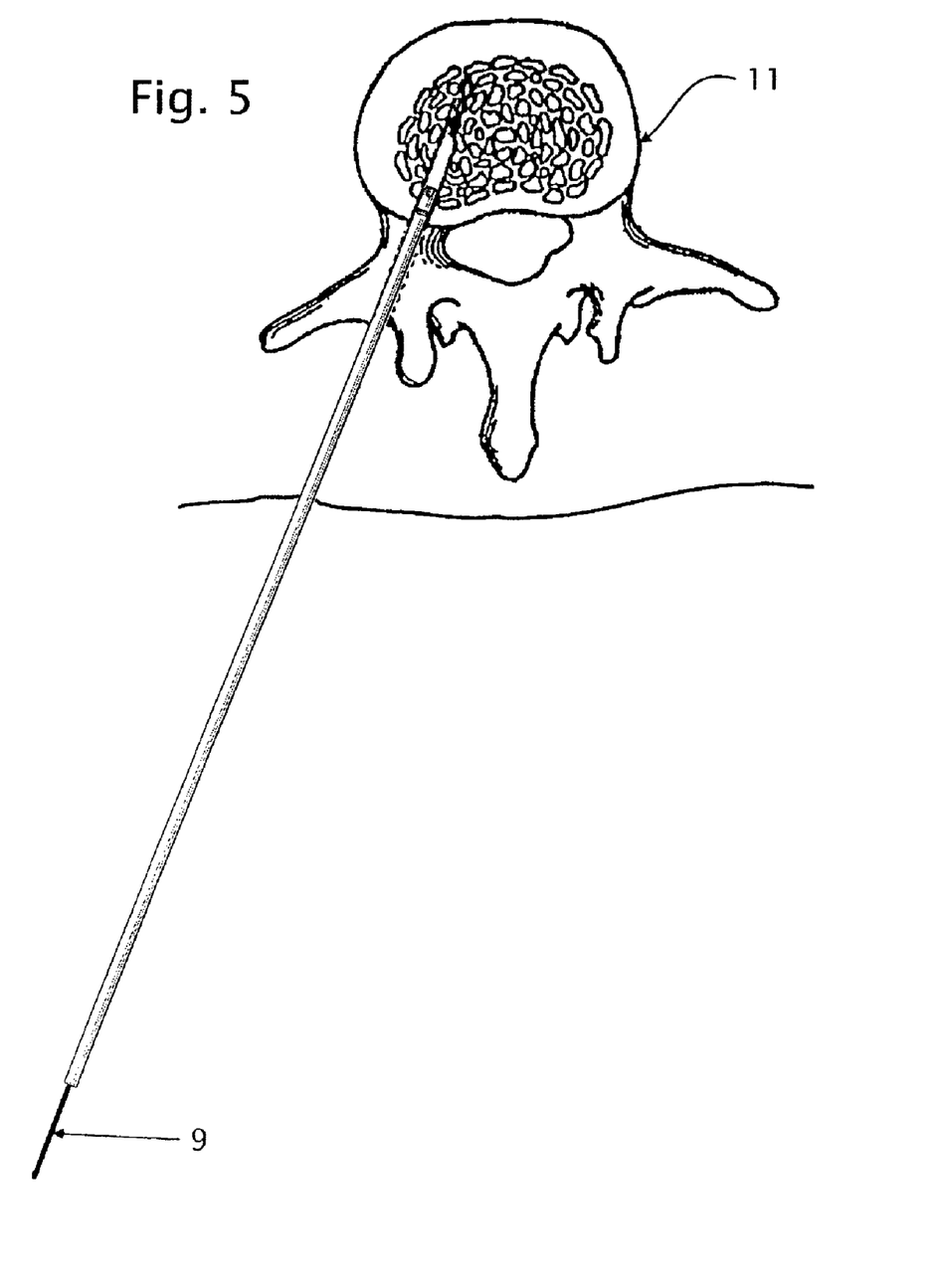
FIG. 5 is a simplified kyphoplasty example illustrating the application of the guide wire introducer in a vertebral application.
Figure 6:
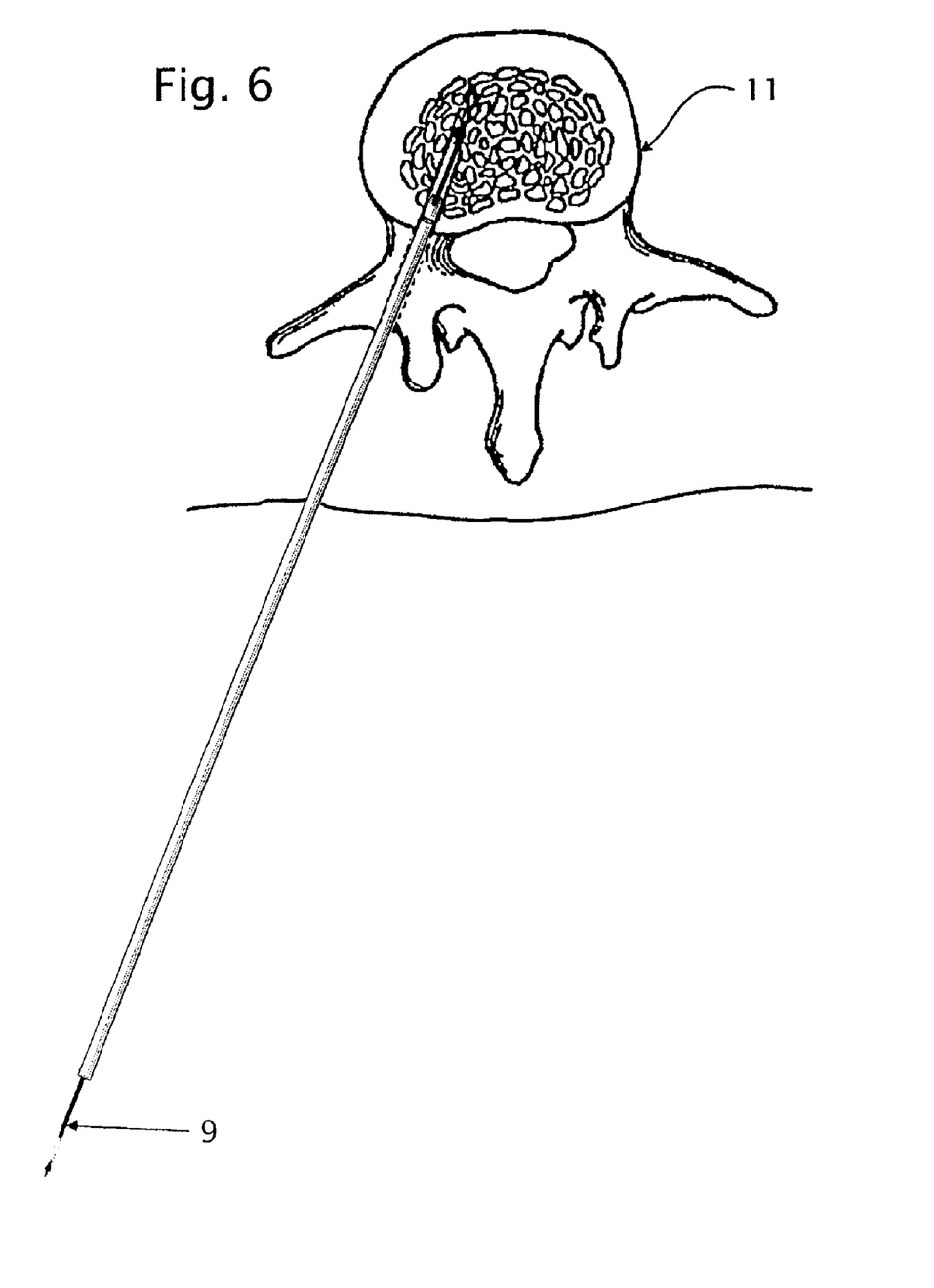
FIG. 6 is a simplified kyphoplasty example illustrating the application of the guide wire introducer in a vertebral application with a surgical guide wire being introduced through its distal tip.

The chamfered tip 2 of the introducer 1 includes end portions 26 and 28 of walls 12 and 14, respectively, which are tapered toward each other. A slit 7 is formed in the end portion 26 of wall 12. Within a preferred application such as the correction of compression fracture induced kyphosis, the introducer 1 is placed {after formation of a pilot hole if necessary} with the guide wire 9 within and not protruding markedly beyond the chamfered tip 2. The guide wire placed within the introducer will have preformed bends in strategic directions and length intervals 10 to allow the guide wire to slip into the chamfered tip integrated slit 7 as these strategic intervals of the guide wire are advanced within range of the integrated slit 7, thus allowing radial steering function when the guide wire slips within the slit after a strategic interval of axial advancement, as indicated in FIGS. 4b and 4c. During such strategic intervals of axial advancement of the guide wire, as a strategically placed preformed bend in the guide wire advances 0.5 to 1 mm proximal to the integrated slit 7, the guide wire then becomes entrapped within the slit of the chamfered tip. This occurrence of guide wire entrapment enables radial manipulation by the introducer in a radial clockwise or counter clockwise fashion via rotation of the introducer about its long axis. At this point of guide wire advancement, the introducer tip integrated slit 7 will continue to entrap the guide wire to enable radial manipulation until the wire is either advanced or retracted from its current position within the introducer or forced out of the tip slit 7. After subsequent axial advancement or retraction of the guide wire within the introducer, the radial steering function of the introducer tip is then reduced or disabled as the guide wire bend moves beyond the position of the integrated slit 7. An illustration of the introducer implementation can be seen in the simplified kyphoplasty example shown in FIGS. 5 and 6.

In addition to the specific function/uses indicated above, the device described herein would also be well suited for use in treating and/or reinforcing weakened, diseased and/or fractured bones in various locations throughout the body. For example, the disclosed device could be used to facilitate the delivery of reinforcing materials and/or medications, such as cancer drugs, replacement bone cells, collagen, bone matrix, demineralized calcium, and other materials/medications, directly into a fractured, weakened and/or diseased bone, thereby increasing the efficacy of the materials, reinforcing the weakened bone and/or speed healing. Moreover, using the steerable guide wire introducer to facilitate targeted injection of such materials into one bone within a body could permit the medication/material to migrate and/or be transported to other bones and/or organs in the body through strategically locating guide wire apparatus, thereby improving the quality of bones and/or other organs not directly injected with the materials and/or medications.

Other embodiments and uses of the invention will be apparent to those skilled in the art from consideration of the specification and practice of the invention disclosed herein. All documents referenced herein are specifically and entirely incorporated by reference. The specification and example should be considered exemplary only, with the true scope and spirit of the invention indicated by the following claims. As will be easily understood by those of ordinary skill in the art, variations and modifications of each of the disclosed embodiments can be easily made within the scope of this invention as defined by the following claims.

What is claimed is:

1. A guide wire introducer and steerable surgical guide wire comprising:

a tubular structure, said tubular structure being elongate, said tubular structure having a proximal end and a distal end, a first substantially flat wall and a second substantially flat wall, said first and said second substantially flat walls each having a surface, each surface having a longitudinal and a lateral dimension, said first and said second substantially flat walls extending between said proximal and said distal end of said tubular structure, being substantially parallel to each other, and being spaced apart from each other, a substantially U-shaped slit at a distal end of one of said substantially flat walls extending from said distal end toward said proximal end of said substantially flat wall;

a guide wire positioned within said tubular structure, said guide wire being movably positioned between said substantially flat walls, said guide wire extending past both said distal end and said proximal end of said tubular structure, said guide wire having at least one preformed bend along the length of said guide wire, said bend providing a guide wire pressure exerted along a portion of the inner surfaces of said first and said second substantially flat walls whereby when said bend contacts said substantially U-shaped slit a portion of said guide wire distal to said bend spontaneously moves into a lower portion of said slit, said preformed bend enabling said guide wire to move in a lateral direction with respect to the length of said guide wire, said slit in one of said first and said second walls of said tubular structure cooperating with said bend in said guide wire to change the direction of travel of said guide wire after it passes said distal end of said tubular structure and to allow rotation of said guide wire as said tubular structure is rotated.

2. The guide wire introducer and steerable surgical guide wire of claim 1 wherein said tubular structure has a chamfer at its distal end.

3. The guide wire introducer and steerable surgical guide wire of claim 1 wherein at least one of said substantially flat walls has a notch proximate said distal end of said tubular structure, a said notch contains a device which enables said notch to be visible under fluoroscopy or X-rays.

4. The guide wire introducer and steerable surgical guide wire of claim 3 wherein said device comprises a radiolucent material.

* * * * *